United States Patent [19]
Meybeck et al.

[11] Patent Number: 5,663,160
[45] Date of Patent: Sep. 2, 1997

[54] COSMETIC OR DERMATOLOGICAL COMPOSITION CONTAINING AT LEAST ONE SAPONIN OF THE GINSENOSIDE TYPE, AND ITS APPLICATIONS, ESPECIALLY FOR TREATING THE HAIR

[75] Inventors: Alain Meybeck; Frederic Bonte, both of Courbevoie; Marc Dumas, Colombes, all of France

[73] Assignee: LVMH Recherche, Nanterre, France

[21] Appl. No.: 387,824

[22] PCT Filed: Sep. 17, 1993

[86] PCT No.: PCT/FR93/00899

§ 371 Date: May 5, 1995

§ 102(e) Date: May 5, 1995

[87] PCT Pub. No.: WO94/06402

PCT Pub. Date: Mar. 31, 1994

[30] Foreign Application Priority Data

Sep. 17, 1992 [FR] France .................................... 92 11104

[51] Int. Cl.$^6$ ............................................. A61K 31/56
[52] U.S. Cl. ............................................. 514/182
[58] Field of Search ........................ 424/70.1, 74, 195.1; 514/729, 880, 182

[56] References Cited

U.S. PATENT DOCUMENTS

| | | | |
|---|---|---|---|
| 2,206,607 | 7/1940 | Jordhoy | 270/47 |
| 2,248,241 | 7/1941 | Kondo | 546/31 |

FOREIGN PATENT DOCUMENTS

| | | |
|---|---|---|
| 2106097 | 9/1992 | Canada . |
| 0-272-920 | 6/1988 | European Pat. Off. . |
| 92 16186 | 10/1992 | WIPO . |

OTHER PUBLICATIONS

Liu et al., "Recent Advances on Ginseng Research in China", *Journal of Ethnopharmacology*, vol. 36 (1992), pp. 27–38.

Morita et al., "Chemical and Morphological Study on Chinese Panax japonicus C.A. Meyer (Zhujie–Shen)", *Chem. Pharm. Bull.*, vol. 31(9) (1983), pp. 3205–3209.

*Acta Botanica Yunnanica*, vol. 1 (1988), pp. 47–62.

"Chemical and Morphological Study on Chinese Panax Japonicus", by C.A. Meyer, Chem. Pharm. Bull., vol. 31, No. 9, pp. 3205–3209, Feb. 18, 1983.

Chemical Abstracts, vol. 103, No. 3, Jul. 22, 1985, abstract No. 16852k, "Ginseng Saponins as Stimulators of Hair Growth", (JP, A, 60 038 314, Feb. 27, 1985).

Chemical Abstracts, vol. 115, No. 22, Dec. 2, 1991, abstract No. 239325, by T. Minabe et al, "Hair Growth–Stimulating Preparations Containing Camp, Pyruvic Acid, Fermentation Metabolites, and Natural Products", (JP,A,3 167 113, Jul. 19, 1991).

Chemical Abstracts, vol. 115, No. 22, Dec. 2, 1991, abstract No. 239293c, by H. Tanaka et al, "Effect of Panax Ginseng on the Production of Glycosaminoglycans in Cultured Human Skin Fibroblast" (Fragance J., vol. 19, No. 8, 1991, pp. 90–92).

Chemical Abstracts, vol. 113, No. 16, Oct. 15, 1990, abstract No. 138316r, by K. Kumazawa, "Hair Growth Stimulating Preparations Containing Lysozyme Chloride", (JP,A,2 157 212, Jun. 18, 1990).

Patent Abstracts of Japan, vol. 11, No. 300, C–449, Sep. 29, 1987 (JP,A,62 093 217, Oct. 18, 1985).

*Primary Examiner*—James J. Seidleck
*Assistant Examiner*—Michael A. Williamson
*Attorney, Agent, or Firm*—Lowe, Price, LeBlanc & Becker

[57] ABSTRACT

The invention relates to a cosmetic or dermatological composition.

This composition contains, as active ingredient, a saponin of formula (I):

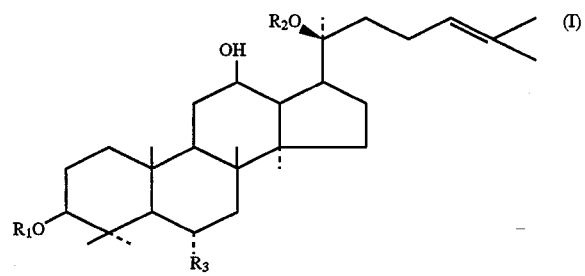

in which:

$R_1$=-Glc(2-1)Glc, $R_2$=-Glc(6-1)Glc and $R_3$=H, the saponin being called G—Rb$_1$, Glc denoting a β-D-glucopyranosyl group, or a plant extract in which it is present, and, if appropriate, cepharanthine or oxyacanthine, or a derivative thereof, or a plant extract in which it is present, such as an extract of *Stephania cepharantha* or *Berberis*.

This cosmetic or dermatological composition is intended in particular for promoting hair growth.

26 Claims, No Drawings

COSMETIC OR DERMATOLOGICAL COMPOSITION CONTAINING AT LEAST ONE SAPONIN OF THE GINSENOSIDE TYPE, AND ITS APPLICATIONS, ESPECIALLY FOR TREATING THE HAIR

This application is a 371 of PCT/FR93/00899 filed Sep. 17, 1993.

The present invention relates to a novel cosmetic or dermatological composition containing at least one saponin of the ginsenoside type and to its applications, especially for treating the hair.

Saponins, especially those derived from plants of the Panax type, have formed the subject of numerous studies. The article published in Chem. Pharm. Bull., 31, 9, 3205–3209 (1983) presents a chemical and morphological study of saponins derived from the rhizomes of *Panax japonicus* harvested in China, and compares them with those derived from the Japanese species. In particular, it demonstrates the important difference in saponin composition between the species.

Among the studies dedicated to saponins, especially those of the ginsenoside type, very particular mention may be made of a recent study published in Journal of Ethnopharmacology, 36, (1992), 27–38, which brings together chemical researches carried out on ginseng. In particular, said article cites various pharmacological activities of ginsengs, especially those of *Panax notoginseng* or San-chi (product I in Tables 1 and 2), and the physicochemical parameters of the different ginsenosides (cf. Table 4).

The Applicant carried out a comparative study of the effect of different saponins and showed, in particular, the value of the saponins of San-chi compared with those of ginseng.

This study led the Applicant to discover that novel cosmetic or pharmaceutical compositions containing a saponin of the ginsenoside type called G—Rb$_1$, of the following structure:

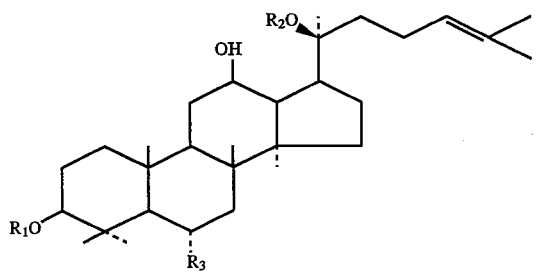

in which:
R$_1$=Glc(2–1)Glc,
R$_2$=Glc(6–1)Glc and
R$_2$=H, where Glc denotes a β-D-glucopyranosyl group, exhibit a particularly valuable activity for arresting and/or slowing down hair loss. The Applicant also discovered that this saponin could advantageously be combined with other saponins, especially with saponins present in Panax notoginseng or San-chi.

The Applicant moreover discovered that particularly advantageous effects as regards the limitation of hair loss and/or renewed hair growth were obtained when the saponin G—Rb$_1$, whether or not in combination with the other saponins mentioned above, was associated with cepharantine or oxyacanthine in the cosmetic or pharmaceutical composition.

Thus, according to a first feature, the present invention relates to a cosmetic or dermatological composition intended in particular for promoting hair growth, characterized in that it contains, as active ingredients, a saponin of the ginsenoside type called G—Rb$_1$, of formula (I):

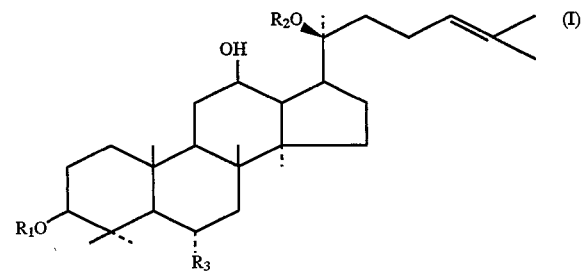

in which:
R$_1$=-Glc(2-1)Glc,
R$_2$=-Glc(6-1)Glc and
R$_3$=H, the saponin being called G—Rb$_1$, Glc denotes a β-D-glucopyranosyl group, and cepharanthine or oxyacanthine, or a derivative thereof, or a plant extract in which it is present, such as an extract of *Stephania cepharantha* or Berberis.

In one variant of the invention, the concentration of saponin G—Rb$_1$ is between 0.001% and 2% and preferably between 0.02 and 2% by weight, based on the total weight of the composition.

In another variant of the invention, the composition also contains at least one other saponin of formula (I) given above:

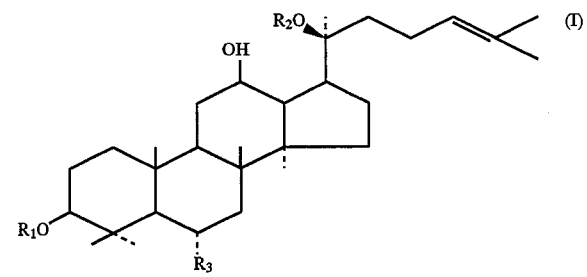

in which:
R$_1$=-Glc(2-1)Glc, R$_2$=-Glc and R$_3$=H, the saponin being called G-Rd, or R$_1$=-Glc, R$_2$=-Glc(6-1)Glc and R$_3$=H, the saponin being called Gy-XVII, or R=-Glc(2-1)Glc, R$_2$=-Glc(6-1)Glc(6–1)Xyl and R$_3$=H, the saponin being called N—R$_4$, or R$_1$=H, R$_2$=-Glc and R$_3$=—O-Glc(2-1)Rha, the saponin being called G—Re, or R$_1$=H, R$_2$=-Glc and R$_3$=—O-Glc, the saponin being called G-Rg$_1$, or R$_1$=H, R$_2$=H and R$_3$=—O-Glc, the saponin being called G—Rh$_1$, or R$_1$=H, R$_2$=-Glc and R$_3$=—O-Glc(2–1)Xyl, the saponin being called N—R$_1$, Glc, Xyl and Rha respectively being a β-D-glucopyranosyl, β-D-xylopyranosyl and α-L-rhamnopyranosyl group.

The abovementioned saponins of formula (I) are used in the literature and for the most part are commercially available. They are marketed in particular by EXTRA SYNTHESE (FRANCE).

They can also be introduced into the cosmetic or dermatological composition in the form of a mixture of saponins, which can be a plant extract, or in the form of a plant extract containing such a mixture.

Thus, in another variant, the abovementioned composition contains, as active ingredient, a mixture of saponins extracted from *Panax notoginseng* or San-chi, in particular from roots or corms.

In one particular variant, the abovementioned composition contains, as active ingredient, a mixture of saponins containing:

from 2% to 60% by weight of saponin G—$Rb_1$
from 10% to 60% by weight of saponin G-$Rg_1$ based on the total weight of saponins in said mixture.

In another particular variant, the abovementioned composition contains, as active ingredient, a mixture of saponins containing:

from 10% to 60% by weight of saponin G—$Rb_1$
from 2% to 60% by weight of saponin G-$Rg_1$ based on the total weight of saponins in said mixture.

In another variant, the abovementioned composition contains, as active ingredient, a mixture of saponins containing:

from 2 to 60% by weight of saponin G—$Rb_1$
from 2 to 60% by weight of saponin G-$Rg_1$
from 0 to 15% by weight of saponin G-Rd
from 0 to 15% by weight of saponin N—$R_1$
from 1 to 10% by weight of saponin G—Re based on the total weight of saponins in said mixture.

In yet another variant, the abovementioned composition contains, as active ingredient, a mixture of saponins containing:

from 10% to 60% by weight of saponin G—$Rb_1$
from 10% to 60% by weight of saponin G-$Rg_1$
has
from 0% to 15% by weight of saponin G-Rd
from 0% to 15% by weight of saponin N—$R_1$
from 1% to 10% by weight of saponin G—Re based on the total weight of saponins in said mixture.

According to a second feature, the present invention also covers a cosmetic or dermatological composition intended in particular for promoting hair growth, characterized in that it contains, as active ingredient, a plant extract containing at least one saponin of formula (I):

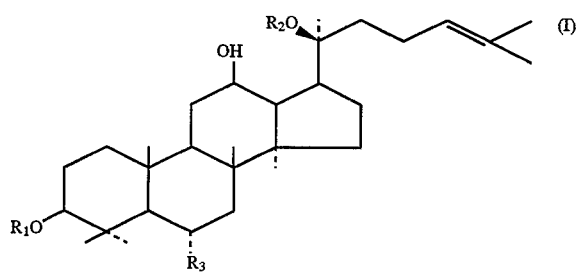

in which:
$R_1$=-Glc(2-1)Glc,
$R_2$=-Glc(6-1)Glc and
$R_3$=H, the saponin being called G—$Rb_1$, Glc denotes a β-D-glucopyranosyl group, and in which the proportion of saponin G—$Rb_1$ in the plant extract is between 2 and 60%, preferably from 10 to 60% and particularly preferably from 20 to 60% by weight, based on the total weight of said extract.

In another variant, the plant extract also contains at least one other saponin of formula (I) given above in which:

$R_1$=-Glc(2-1)Glc, $R_2$=-Glc and $R_3$=H, the saponin being called G-Rd, or $R_1$=-Glc, $R_2$=-Glc(6-1)Glc and $R_3$=H, the saponin being called Gy-XVII, or $R_1$=-Glc(2-1)Glc, $R_2$=-Glc(6-1)Glc(6-1)Xyl and $R_3$=H, the saponin being called N—$R_4$, or $R_1$=H, $R_2$=-Glc and $R_3$=—O-Glc(2-1)Rha, the saponin being called G—Re, or $R_1$=H, $R_2$=-Glc and $R_3$=—O-Glc, the saponin being called G-$Rg_1$, or $R_1$=H, $R_2$=H and $R_3$=—O-Glc, the saponin being called G—$Rh_1$, or $R_1$=H, $R_2$=-Glc and $R_3$=—O-Glc(2-1)Xyl, the saponin being called N—$R_1$, Glc, Xyl and Rha respectively being a β-D-glucopyranosyl, β-D-xylopyranosyl and α-L-rhamnopyranosyl group.

In another variant, the plant extract contains:

from 2% to 60% by weight of saponin G—$Rb_1$
from 2% to 60% by weight of saponin G-$Rg_1$
from 0% to 15% by weight of saponin G-Rd
from 0% to 15% by weight of saponin N—$R_1$
from 1% to 10% by weight of saponin G—Re based on the total weight of the extract.

In one variant, the plant extract contains:

from 10% to 60% by weight of saponin G—$Rb_1$
from 10% to 60% by weight of saponin G-$Rg_1$
from 0% to 15% by weight of saponin G-Rd
from 0% to 15% by weight of saponin N—$R_1$
from 1% to 10% by weight of saponin G—Re based on the total weight of the extract.

In yet another variant, the abovementioned composition is characterized in that the plant extract is an extract of *Panax notoginseng* or San-chi, preferably an extract of roots or corms.

In yet another variant common to the two features mentioned above, the composition is characterized in that the total concentration of abovementioned saponins or abovementioned plant extract is between 0.001% and 2% by weight, based on the total weight of the composition.

In another variant, the concentration of abovementioned plant extract is between 0.1 and 2% by weight, based on the total weight of the composition.

In yet other particularly advantageous variants, the compositions also contain cepharanthine or oxyacanthine, or a derivative thereof, or a plant extract in which it is present, such as an extract of *Stephania cepharantha* or Berberis.

Moreover, the different particular variants described below are applicable to the different features of the invention. Thus, in one of these variants, the compositions contain from 0.001 to 2% by weight of cepharanthine or oxyacanthine, or a derivative thereof, or a plant extract in which it is present.

In another particular variant, the concentration of cepharanthine or oxyacanthine, or a derivative thereof, in the composition is approximately equal to or less than that of the abovementioned saponin or saponins, in particular up to 10 times less than the latter concentration.

In one variant, the cosmetic or dermatological composition according to the invention also comprises an effective concentration of at least one other active substance selected from quinine or derivatives thereof, rubefacients such as methyl nicotinate, a papilla fibroblast culture supernatant such as that defined in the document EP-A-272.920, keratin hydrolyzates, trace elements such as zinc, selenium and copper, 5-α-reductase inhibitors such as progesterone and cyproterone acetate, azelaic acid and derivatives thereof, a 4-methyl-4-azasteroid, in particular 17-β-N,N-diethylcarbamoyl-4-methyl-4-aza-5-α-androstan-3-one, or else an extract of Serenoa repens.

In another variant, the compositions of the invention also contain hyaluronic acid, preferably at a concentration of between 0.01 and 1% by weight.

In one particular embodiment of the invention, the plant extract containing the abovementioned saponins of formula (I) is obtained by the process which is described below by way of indication, but without implying any limitation. The dry matter is extracted with a solvent selected from the group consisting of water, alcohols preferably containing from 1 to 4 carbon atoms and organic esters preferably containing from 3 to 6 carbon atoms, or with a mixed solvent based on any mixture of the abovementioned solvents.

Advantageously, the primary extraction solvent is methanol, ethanol, a methanol/water mixture or an ethanol/water mixture.

The ratio of plant matter to extraction agent is not critical and will generally be between 1:5 and 1:20 parts by weight.

The abovementioned primary extraction is carried out at temperatures between room temperature and the boiling point of the solvent used for the extraction.

Preferably, the primary extraction is carried out under reflux at atmospheric pressure for a period of 2 to 4 h. Moreover, it is advantageously preceded by cold maceration for 2 to 4 h in the extraction solvent.

When the extraction is complete, the solvent phase containing the extract is filtered and then concentrated and/or evaporated to dryness under reduced pressure to give a first saponin-rich extract according to the invention.

In one particular variant, the use according to the invention relates to a mixture of abovementioned saponins. A mixture of saponins according to the invention is obtained in particular from the abovementioned first concentrated or dry extract by following the procedure indicated below. The abovementioned first extract is introduced and then stirred into an apolar solvent which is preferably miscible with the primary extraction solvent, said apolar solvent being for example a low-molecular ether or ketone, in particular ethyl or isopropyl ether, acetone or methyl ethyl ketone. The amount of apolar solvent by weight is generally 5 to 100 parts per part of primary extract. The insoluble material and/or the precipitate formed mainly contains a mixture of saponins according to the invention.

Advantageously, the mixture of saponins obtained above is purified by any process accessible to those skilled in the art.

In particular, the abovementioned insoluble material and/or precipitate is redissolved in about 20 times its own weight of water. The aqueous solution is then extracted 3 to 4 times with a sparingly water-soluble alcohol such as butanol, saturated with water, for example in proportions of 1:1 by volume for each extraction operation. The alcohol phases are combined and evaporated under reduced pressure. The residue is dissolved in about 10 times its own weight of water and the solution is then dialyzed against pure water for 4 to 5 days. The contents of the dialysis cell are lyophilized. If appropriate, the purification of the resulting mixture of saponins can be further improved by dissolving the lyophilizate in methanol and then discharging the solution into ethyl ether. The precipitate formed is collected. The saponins can also be extracted from plant tissues in culture (in vitro culture of roots or calluses).

If the cosmetic composition according to the invention contains cepharantine, the latter is advantageously obtained by extraction from plant of the genus Stephania, in particular Stephania tetrandra, Stephania cepharanta, Stephania epigeae, Stephania sinica, Stephanie delayavii, Stephania sasakii hayata or Stephania erecta, using methods described for example in U.S. Pat. No. 2,206,607 and U.S. Pat. No. 2,248,241.

According to another feature, the invention also covers the use of a composition as defined above for promoting hair growth and/or slowing down hair loss, especially in the treatment of androgenogenetic alopecia, for treating the skin, in particular for restoring, preserving and/or strengthening the protective function of the skin, especially the water barrier function, for regenerating the epidermis or for preventing or treating wrinkles.

The cosmetic or dermatological compositions according to the present invention can be applied topically for the activity stated above, in particular in compositions presented in the form of a cream, gel or lotion and intended for application to the scalp.

According to another feature, the present invention also provides a method of treatment intended for promoting hair growth, slowing down hair loss, especially in the treatment of androgenogenetic alopecia, or combating pruritus, especially pruritus of the scalp, for treating the skin, in particular for restoring, preserving and/or strengthening the protective function of the skin, especially the water barrier function, for regenerating the epidermis or for preventing or treating wrinkles, characterized in that it comprises applying, to the area to be treated, at least one saponin of formula (I) given above, or a plant extract in which it is present, in an amount effective for achieving said desired effect, said saponin or said extract optionally being associated with cepharantine or oxyacanthine, or a derivative thereof, or with a plant extract in which it is present, such as an extract of Stephania cepharantha or Berberis.

According to another feature, the invention also provides a process for the manufacture of a cosmetic or dermatological composition intended in particular for stimulating hair growth, slowing down hair loss, especially in the treatment of androgenogenetic alopecia, or combating pruritus, especially pruritus of the scalp, for treating the skin, in particular for restoring and preserving and/or strengthening the protective function of the skin, especially the water barrier function, for regenerating the epidermis or for preventing or treating wrinkles, characterized in that it comprises using saponin of formula (I) or a plant extract in which it is present, said saponin or said plant extract optionally being associated with cepharantine or oxyacanthine, or a derivative thereof, or with a plant extract in which it is present, such as an extract of Stephania cepharantha or Berberis, which is mixed with a dermatologically or cosmetically acceptable excipient, vehicle or carrier.

In other variants, the diverse variants which have been stated above for the other features of the invention are used.

The percentages are given by weight, unless indicated otherwise. The Examples which follow are given by way of illustration and without implying any limitation of the present invention.

EXAMPLE 1

Demonstration of the value of the saponins of San-chi and comparison with those of *Panax ginseng*

The individual activity of saponins of San-chi and a mixture of saponins extracted from San-chi, compared with a saponin G—Rc present in abundance in *Panax ginseng*, was tested on a transformed human keratinocyte line.

The following protocol was adopted:
D=1: inoculation of 50,000 cells/dish in EMEM+1% FCS,
D=0: change of medium+addition of test products,
D=6: cell counting.
The results are collated in Table 1 below.

TABLE 1

| Product | μg/ml | Activity | Statistics |
|---|---|---|---|
| G-Rb$_1$ | 25 | +4.4 | NS |
|  | 50 | +5.6 | NS |
|  | 100 | +17.7 | S |
| G-Rd | 25 | −2.4 | NS |
|  | 50 | +8.6 | NS |
|  | 100 | −25.6 | S |
| G-Re | 25 | +1.5 | NS |
|  | 50 | +7.6 | NS |
|  | 100 | +9.7 | NS |
| G-Rg$_1$ | 25 | −6 | NS |
|  | 50 | −4.9 | NS |
|  | 100 | +4.1 | NS |
| San-chi saponins | 25 | −2.3 | NS |
|  | 50 | +3.8 | NS |
|  | 100 | +11.5 | S |
| G-Rc | 25 | +16.3 | NS |
|  | 50 | −30.2 | S |
|  | 100 | −97.0 | S |

It is therefore apparent that Rb$_1$ is responsible for the promitotic activity.

These data become particularly interesting and fundamental when put side by side with the ginsenoside composition of San-chi compared with white ginseng.

The values given in a very recent publication in Acta Botanica Yunnanica, 1988, I, 47–62, are as follows (in %):

| Ginsenosides | San-chi | White ginseng |
|---|---|---|
| G-Rb$_1$ | 1.8 | 0.47 |
| G-Rd | 0.2 | 0.15 |
| G-Re | 0.15 | 0.15 |
| G-Rg$_1$ | 1.9 | 0.21 |
| G-Rc | — | 0.26 |

(White ginseng is a root of *Panax ginseng*, which is simply peeled and dried.)

This Table shows that although the proportion of cytotoxic Rd is similar, that of the ginsenoside Rb$_1$, which is responsible for the activity, is 4 times greater in San-chi. This confirms the value of specifically choosing San-chi rather than Panax ginseng. Furthermore, white ginseng contains about 0.6 of G-Rc, which is very cytotoxic, whereas San-Chi contains virtually none.

EXAMPLE 2

Dermatological lotion for treating androgenogenetic alopecia

A lotion (called A) according to the invention is prepared which contains:

| Absolute alcohol | 32.00 g |
|---|---|
| Butylhydroxyanisole | 0.001 g |
| Cepharantine | 0.10 g |
| Saponins of Panax notoginseng (San-chi) | 0.10 g |
| Eau sauvage ® | 0.35 g |
| Ceraphyl 60 ® | 0.08 g |
| Cremophor Rh 40 ® | 0.40 g |
| Aqueous excipient qsp | 100 g |

EXAMPLE 3

Tonic lotion for combating hair loss according to the invention

This lotion corresponds to the following formulation with the proportions by weight indicated below:

| Cepharantine | 0.15 g |
|---|---|
| Ginsenoside Rb$_1$ | 0.20 g |
| BHA | 0.05 g |
| Ceraphyl 60 ® | 0.07 g |
| Cremophor RH$_4$O | 0.5 g |
| Ethanol | 35 g |
| Hyaluronic acid | 0.1 g |
| Perfumed aqueous exceipient qsp | 100 g |

EXAMPLE 4

Preparation of a styling lotion for combating hair loss according to the invention A composition is prepared which corresponds to the following formulation with the proportions by weight given below:

| Cepharantine | 0.1 g |
|---|---|
| Saponins of Panax notoginseng | 0.12 g |
| Propylene glycol | 3.00 g |
| Cremophor RH$_4$O | 0.5 g |
| Panthenol | 0.1 g |
| Ethanol | 32 g |
| Perfumed aqueous excipient qsp | 100 g |

EXAMPLE 5

Preparation of a medicated gel for combating hair loss, dandruff and pruritus

A mixture of saponins, called S below, containing the following proportions by weight:

| G-Rb$_1$ | 2 |
|---|---|
| G-Rd | 0.2 |
| G-Re | 1 |
| G-Rg$_1$ | 2 |
| N-R$_1$ | 0.2 | is used to prepare the gel corresponding to the formulation below, in which the amounts are expressed by weight:

| Cepharantine | 0.05 g |
|---|---|
| Mixture S | 0.02 g |
| Ethanol | 30 g |
| Cremophor RH$_4$O ® | 0.5 g |
| 2% Carbopol 980 ® gel | 50 g |
| Aqueous excipient qsp | 100 g |

This gel is applied 3 times a week, preferably in the evening for 15 min by massaging. Rinsing with water.

EXAMPLE 6

After-shave tonic lotion

| Extract of Panax notoginseng | 0.05 g |
|---|---|
| Cepharanthine | 0.05 g |
| 90 v/v alcohol | 30.— g |

| | |
|---|---|
| Alpha-bisabolol | 0.1 g |
| Perfumed aqueous excipient qsp | 100.— g |

EXAMPLE 7

Anti-wrinkle emulsion

| | |
|---|---|
| Ginsenoside G-Rb$_1$ | 0.6 g |
| Oxyacanthine | 0.1 g |
| Emulsifying excipient qsp | 100 g |

EXAMPLE 8

Firming body milk

| | |
|---|---|
| Ginsenoside G-Rb$_1$ | 0.1 g |
| Ginsenoside G-Rg$_1$ | 0.1 g |
| Excipient for milk, qsp | 100.— g |

EXAMPLE 9

Shampoo for stimulating hair growth

| | |
|---|---|
| Saponin of Panax notoginseng | 0.3 g |
| Copra diethanolamine | 2 g |
| Sodium lauryl ether sulfate | 0.5 g |
| Alkyl glucoside | 15.— g |
| Methyl parahydroxybenzoate | 0.5 g |
| Perfumed aqueous excipient, qsp | 100.— g |

EXAMPLE 10

Clinical study of a composition according to the invention

The study is carried out on Composition A of Example 2. The results are compared with those obtained with a placebo consisting of a composition identical to A but containing neither cepharantine nor extract of San-chi.

1. Experimental protocol

Inclusion criteria

Healthy male volunteers suffering from chronic and substantial hair loss, selected at random during the scalp consultation.

Age limits:

21–44 years for the lotion, average age 33.3 years

22–45 years for the placebo, average age 34.2 years

Posology and administration

Lotion A and its placebo were applied twice a day at a rate of 7 sprays each time, continuously for 6 months, especially on the top of the head, followed by gentle massaging for a few minutes. There was no associated treatment. 10 lotions and 10 placebos were handed out at random, the expert having no knowledge of the nature of the bottles.

All the subjects were in perfect health.

The stage of their hair loss was graded as follows, according to the Hamilton classification:

| | |
|---|---|
| Stage II | = 1 case |
| Stage III | = 6 cases |
| Stage III vertex | = 5 cases |
| Stage IV | = 7 cases |
| Female-type stage I+ | = 1 case |

2. Analysis of the results

The hair loss was assessed by means of 3 parameters:

the patient's subjective impression, the pulling test, the trichogram.

The subjective impression must be treated with caution because it depends on the anxiety and obsession associated with hair loss.

The pulling test consists in running swatches of hair between 2 fingers at three points on the scalp: vertex, temple and occiput, and pulling with an even force. The number of hairs which pull out are counted. This makes it possible to check the reality of the hair loss.

The trichogram makes it possible to check the action of the product by determining the pilary formula after taking samples of hair from the vertex, temple and occiput.

The pulling tests were performed at 0, 3 months and 6 months.

The trichograms were prepared at 0 and 6 months.

The subjects had an interview and a medical examination at 0, 3 months and 6 months for the purpose of evaluating the severity of the alopecia and its development.

In addition to the effects on actual hair loss, the action of the lotion on accompanying signs was evaluated.

These signs are:

squamous condition or dandruff pruritus.

After 6 months of treatment, the double-blind study carried out on 20 subjects shows a definite action of the lotion on hair loss in man.

The following can also be noted:

a remarkable effect on the squamous condition and pruritus, a pleasant application.

What is claimed is:

1. A topical composition for cosmetic and dermatological application comprising, as active ingredient, of between 0.001 and 2% by weight, based upon the total weight of the composition, of a plant extract containing between about 2% by weight and 60% by weight of at least the saponin denominated G—Rb$_1$ of formula (I):

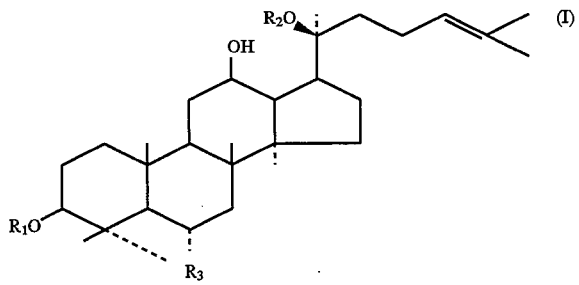

in which:

R$_1$=-Glc(2-1)Glc, R$_2$=-Glc(6-1)Glc and R$_3$=H wherein Glc denotes a β-D-glucopyranosyl group.

2. The composition according to claim 1 characterized in that the plant extract also contains at least one other saponin of formula (I) given above in which:

R$_1$=-Glc(2-1)Glc, R$_2$=-Glc and R$_3$=H, the saponin being called G-Rd, or $R_1$=-Glc, $R_2$=-Glc(6-1)Glc and $R_3$=H, the saponin being called Gy-XVII, or $R_1$=-Glc(2-1)Glc, $R_2$=-Glc(6-1)Glc(6-1)Xyl and $R_3$=H, the saponin being called N—$R_4$, or $R_1$=H, $R_2$=-Glc and $R_3$=—O-Glc(2-1)Rha, the saponin being called G—Re, or $R_1$=H, $R_2$=-Glc and $R_3$=—O-Glc, the saponin being called G-$Rg_1$, or $R_1$=H, $R_2$=H and $R_3$=—O-Glc, the saponin being called G—$Rh_1$, or $R_1$=H, $R_2$=-Glc and $R_3$=—O-Glc(2-1)Xyl, the saponin being called N—$R_1$, Glc, Xyl and Rha respectively being a β-D-glucopyranosyl, β-D-xylopyranosyl, and α-L-rhamnopyranosyl group.

3. The composition according to claim 2 characterized in that the plant extract contains:

from 2 to 60% by weight of saponin G—$Rb_1$ from 2 to 60% by weight of saponin G-$Rg_1$ from 0 to 15% by weight of saponin G-Rd from 0 to 15% by weight of saponin N—$R_1$ from 1 to 10% by weight of saponin G—Re based on the total weight of the extract.

4. The composition according to claim 2, characterized in that the plant extract contains:

from 10% to 60% by weight of saponin G—$Rb_1$ from 10% to 60% by weight of saponin G-$Rg_1$ from 0% to 15% by weight of saponin G-Rd from 0% to 15% by weight of saponin N—$R_1$ from 1% to 10% by weight of saponin G—Re based on the total weight of the extract.

5. The composition according to claim 1 characterized in that the plant extract is an extract of *Panax notoginseng* or San-chi.

6. The composition according to claim 1 characterized in that the concentration of abovementioned plant extract is between 0.1 and 2% by weight, based on the total weight of the composition.

7. The composition according to claim 1 also comprising cepharanthine, oxyacanthine, a derivative thereof, or a plant extract in which said cepharanthine, oxyacanthine or a derivative thereof is present.

8. The composition according to claim 1 further comprising from 0.001 to 2% by weight of cepharanthine, oxyacanthine, a derivative thereof, or a plant extract in which said cepharanthine, oxyacanthine or a derivative thereof is present.

9. The composition according to claim 1 further comprising cepharanthine or oxyacanthine or a derivative thereof, at a concentration in the composition up to approximately equal to that of the total concentration of saponins therein.

10. The composition according to claim 1 also comprising an effective concentration of at least one other active substance selected from the group consisting of quinine and derivatives thereof, rubefacients, a papilla fibroblast culture supernatant, keratin-hydrolyzates, trace elements selected from the group consisting of zinc, selenium and copper, 5-α-reductase inhibitors selected from the group consisting of progesterone and cyproterone acetate, azelaic acid and derivatives thereof, a 4-methyl-4-azasteroid, and an extract of *Serona repens*.

11. The composition according to claim 1 characterized in that it also contains from 0.01% to 1% by weight of hyaluronic acid.

12. A method for strengthening the protective functions of the skin and for retarding and treating wrinkles, which comprises applying, to the area to be treated, a composition according to claim 1 in an amount effective for achieving the indicated effect.

13. A method for retarding and treating wrinkles which comprises applying to the area to be treated a composition according to claim 1 in an amount effective for achieving the indicated effect.

14. A method for promoting hair growth, slowing down hair loss, treating androgenogenetic alopecia, and combating pruritus of the scalp, treating the skin, restoring, preserving and strengthening the protective function of the skin, or retarding and treating wrinkles, wherein said method comprises applying, to the area to be treated, a composition according to claim 1 in an amount effective for achieving said desired effect.

15. A cosmetic or dermatological composition for promoting hair growth, comprising, as active ingredient, an effective amount of an extract of *Panax notoginseng* or San-chi and cepharanthine or oxyacanthine, a derivative thereof, or a plant extract in which said cepharanthine, oxyacanthine or a derivative thereof, is present.

16. The composition according to claim 15 further comprising from 0.001 to 2% by weight of cepharanthine, oxyacanthine, a derivative thereof, or a plant extract in which said cepharanthine, oxyacanthine or derivative thereof is present.

17. The composition according to claim 15 further comprising cepharanthine, oxyacanthine or a derivative thereof, at a concentration in the composition approximately up to equal that of the total concentration of saponins therein.

18. The composition according to claim 15 also comprising an effective concentration of at least one other active substance selected from the group consisting of quinine and derivatives thereof, rubefacients, a papilla fibroblast culture supernatant, keratin hydrolyzates, trace elements selected from the group consisting of zinc, selenium and copper, 5-α-reductase inhibitors selected from the group consisting of progesterone and cyproterone acetate, azelaic acid and derivative thereof, a 4-methyl-4-azasteroid and an extract of *Serenoa repens*.

19. The composition according to claim 15 characterized in that it also contains from 0.01% to 1% by weight of hyaluronic acid.

20. A method for promoting hair growth, slowing down hair loss, treating androgenogenetic alopecia, combating pruritus of the scalp, restoring, preserving and strengthening the protective function of the skin, or for retarding and treating wrinkles, which comprises applying, to the area to be treated, a composition according to claim 15 in an amount effective for achieving the indicated effect.

21. A topical composition for cosmetic and dermatological application consisting essentially, as active ingredient, of between 0.001 and 2% by weight, based upon the total weight of the composition, of a plant extract containing between about 2% by weight and 60% by weight of at least the saponin denominated G—$Rb_1$, of formula (I):

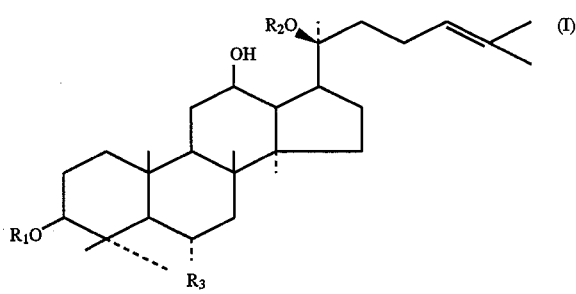

in which:

$R_1$=-Glc(2-1)Glc, $R_2$=-Glc(6-1)Glc and $R_3$=H
wherein Glc denotes a β-D-glucopyranosyl group.

22. A composition consisting essentially of active ingredients of between 0.001 and 2% by weight, based upon the total weight of the composition, of a plant extract consisting essentially of:

from 2 to 60% by weight of saponin G—$Rb_1$, from 2 to 60% by weight of saponin G-$Rg_1$, from 0 to 15% by weight of saponin G-Rd, from 0 to 15% by weight of saponin N—$R_1$, and from 1 to 10% by weight of saponin G—Re based on the total weight of the extract.

23. A composition consisting essentially of active ingredients of between 0.001 and 2% by weight, based upon the total weight of the composition, of a plant extract consisting essentially of:

from 10% to 60% by weight of saponin G—$Rb_1$, from 10% to 60% by weight of saponin G-$Rg_1$, from 0 to 15% by weight of saponin G-Rd, from 0 to 15% by weight of saponin N—$R_1$, and from 1 to 10% by weight of saponin G—Re based on the total weight of the extract.

24. A topical composition for cosmetic and dermatological application consisting essentially, as active ingredient, of between 0.001 and 2% by weight, based on the total weight of the composition, of saponin denominated G—$Rb_1$, of formula (I):

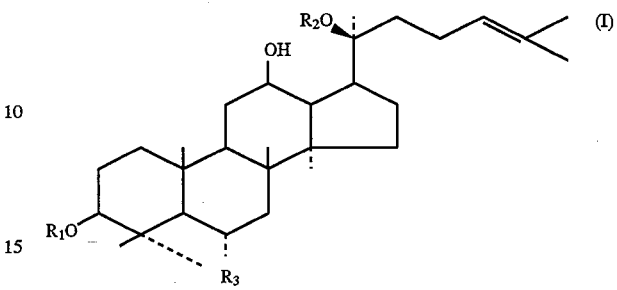

in which:

$R_1$=-Glc(2-1)Glc, $R_2$=-Glc(6-1)Glc and $R_3$=H,
wherein Glc denotes a β-D-glucopyranosyl group in an excipient appropriate for a topical cosmetic and dermatological application.

25. A topical composition for cosmetic and dermatological application consisting essentially of, as active ingredient, between 0.001 and 2% by weight, based on the total weight of the composition, of an extract of *Panax notoginseng* or San-chi in an excipient appropriate for a topical cosmetic and dermatological application.

26. A topical composition for cosmetic and dermatological application consisting essentially of, as active ingredient, from 0.001 and 2% by weight, based on the total weight of the composition, of a plant extract containing from 10% to 60% by weight of saponin G—$Rb_1$ and from 10% to 60% by weight of saponin G—$Rg_1$ based on the total weight of the extract, in an excipient which is appropriate for a topical cosmetic and dermatological application.

* * * * *